United States Patent [19]

L'Esperance, Jr.

[11] Patent Number: 5,263,950
[45] Date of Patent: Nov. 23, 1993

[54] PHACO-EXTRACTOR FOR FRAGMENTING CATARACTOUS-LENS SITUS OF FRAGMENTATION

[75] Inventor: Francis A. L'Esperance, Jr., Englewood, N.J.

[73] Assignee: L'Esperance Medical Technologies, Inc., New York, N.Y.

[21] Appl. No.: 734,940

[22] Filed: Jul. 24, 1991

[51] Int. Cl.$^5$ .............................................. A61B 17/36
[52] U.S. Cl. ...................................... 606/6; 606/2; 606/4; 604/19; 604/27; 604/43; 607/89
[58] Field of Search ..................... 606/6, 4, 7, 13-16, 606/2; 604/19, 21, 27, 35, 43; 128/362, 395, 396, 397

[56] References Cited

U.S. PATENT DOCUMENTS

| | | | |
|---|---|---|---|
| 4,694,828 | 9/1987 | Eichenbaum | 606/6 |
| 4,760,840 | 8/1988 | Fournier, Jr. et al. | 606/15 |
| 4,819,630 | 4/1989 | DeHart | 606/15 |
| 4,846,172 | 7/1989 | Berlin | 606/4 |
| 4,917,084 | 4/1990 | Sinofsky | 606/15 |
| 4,959,063 | 9/1990 | Kojima | 606/15 |
| 4,988,163 | 1/1991 | Cohen et al. | 606/15 |
| 5,123,902 | 6/1992 | Müller et al. | 606/4 |
| 5,129,896 | 7/1992 | Hasson | 606/15 |

FOREIGN PATENT DOCUMENTS 0335714 10/1989 European Pat. Off. ............... 606/6

*Primary Examiner*—Stephen C. Pellegrino
*Assistant Examiner*—Jeffrey A. Schmidt
*Attorney, Agent, or Firm*—Hopgood, Calimafde, Kalil, Blaustein & Judlowe

[57] ABSTRACT

A hand-held phaco-extractor instrument comprises an elongate tubular irrigation/aspiration system for a distal or operating end, wherein a fiber-optic cable delivers laser-irradiation of wavelength which is so substantially coincident with the known high absorptivity in water that laser-energy penetration is essentially limited to the region of cataractous-lens tissue to be fragmented and extracted. In other words, for the aqueous environment in which the particular laser radiation is to do its fragmentation, there is no possibility of damaging radiation penetration to the retina or to other regions of the eye which are irrelevant to the involved cataract-removal surgery.

16 Claims, 1 Drawing Sheet

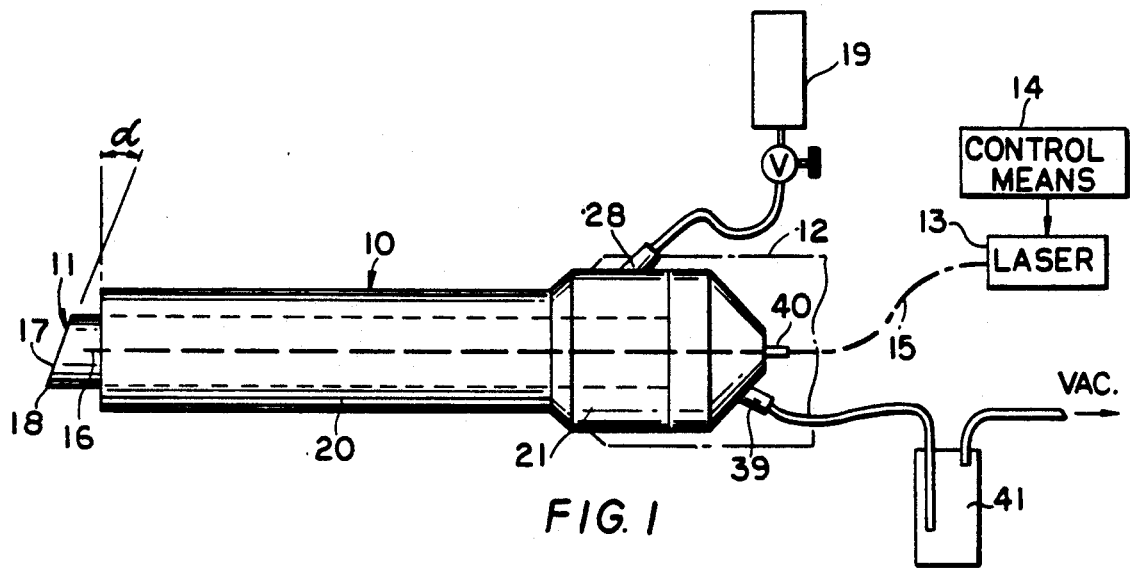
FIG. 1
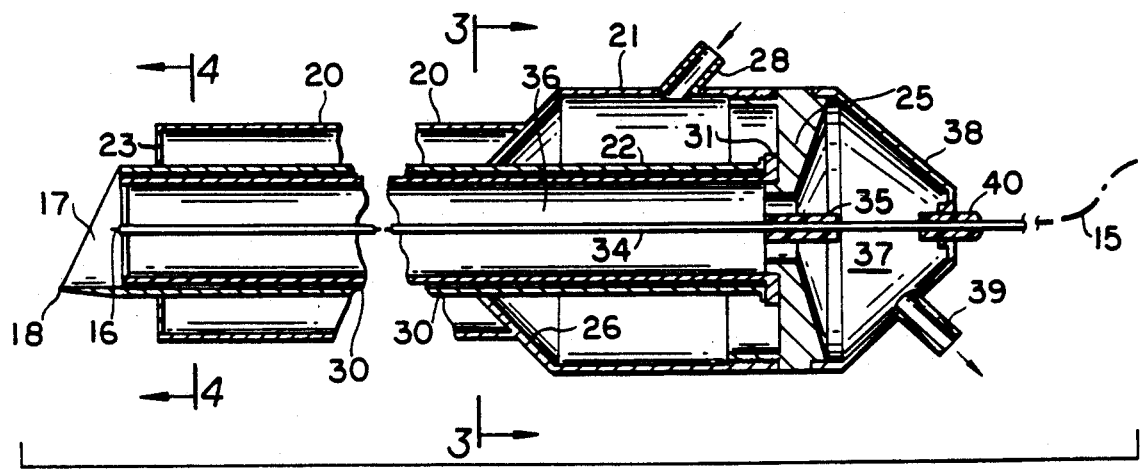
FIG. 2
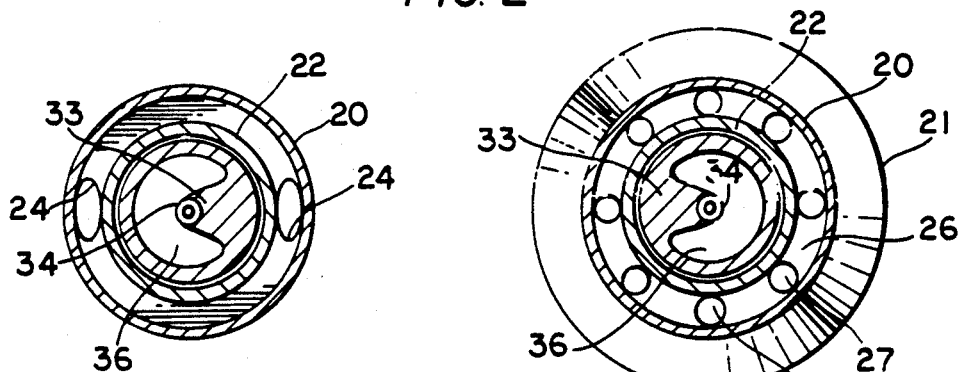
FIG. 4
FIG. 3

PHACO-EXTRACTOR FOR FRAGMENTING CATARACTOUS-LENS SITUS OF FRAGMENTATION

BACKGROUND OF THE INVENTION

The present invention relates to surgically invasive apparatus for accessing a cataracted natural lens via the anterior chamber and a dilated iris, and for removing cataractous material from the lens.

Within the last ten years, there have been important advances in instrumentation and techniques for removal of cataractous-lens material. What has been termed phacoemsulsification is perhaps the most important of these advances, and it should be noted that this term has applied to the use of ultrasonic energy, delivered at the small tip of a piezoelectric or magnetostrictive device; this is the currently favored means of locally fragmenting cataractous tissue, for extraction via a continuous flow of benign liquid. But use of such phacoemulsufication devices calls for great skill, in that excessive delivery or misdirected delivery of ultrasonic energy can result in irreparable damage to the capsulary bag, the retina and/or other parts of the eye.

It has also been proposed, but not generally accepted, to use local delivery of laser radiation to fragment cataractous material, to an extent permitting extraction in a continuous flow of irrigating liquid. But again, there is the prospect of irreversible damage to other parts of the eye, and great surgical skill is required.

To simplify the problem of surgical skill and to reduce the potential for damage through posterior escape of laser radiation, a recently published article* mentions the work of Dr. Patricia E. Bath with her "laserphaco" apparatus, which is said to involve phacoablation, and irrigation and aspiration (I/A). Her apparatus is said to utilize a neodymium-YAG laser (presumably frequency-quadrupled, for ultraviolet-wavelength radiation) or an excimer laser, a laser-phaco probe, a laser-synchronized computer, and a laser interface. The computer is said to sense the high ultraviolet absorbance of the cataracted lens, and the computer selects the correct wavelength; the computer is also said to distinguish between the different refractive indices of the nucleus and the cortex, and to adjust the laser's energy density, thus minimizing the possibility of radiation outside the desired zone. Dr. Bath is quoted as stating that "the computer aims the beam, focuses the beam, tests the beam, and executes ablation of the foci with no escape of radiation posteriorly . . . So what you have coming through a single probe is mapping, focusing, ablation and I/A".
*"Will Laser Become the Cataract Surgery Instrument of the '90's?", *Ophthalmology Times*, Aug. 1, 1990, page 40.

Throughout this case, the terms phacoemulsification, phacoablation, and tissue-fragmentation are deemed to be synonymous, in the sense that they apply to the use of externally supplied and locally delivered energy, whether ultrasonically applied or laser radiation, to break up and reduce cataractous material to a particle size small enough for external removal by the flow of an irrigating liquid in an I/A system.

BRIEF STATEMENT OF THE INVENTION

It is an object of the invention to provide an improved laser-operated apparatus and technique for removal of cataractous-lens tissue.

A specific object is to utilize the known high energy-absorption coefficient of water at a particular wavelength, for so attenuating a phaco-fragmenting laser irradiation as to minimize potential damage to tissue other than cataractous-lens tissue.

Another specific object is to achieve the above objects with an instrument which embodies its own means of infusing and aspirating a flow of liquid at the situs of fragmentation.

The invention achieves these objects in a hand-held instrument having an elongate stem which enables external manipulation at its proximal end and which at its distal end presents a cutter adjacent an open cavity. Within or adjacent to this open cavity, laser radiation from the discharging distal end of an optical fiber is operative only on nearby cataractous-lens tissue to be fragmented. The particular laser is selected for its radiation wavelength such that laser radiation in water and water-containing cataractous-tissue is absorbed within a radiating distance that is at least no greater than the thickness dimension of the cataractous lens upon which the instrument is to operate.

DETAILED DESCRIPTION

Preferred and other embodiments of the invention will be described in detail, in conjunction with the accompanying drawings. In said drawings:

FIG. 1 is a simplified overall view of a phacoemulsifying instrument of the invention, together with external devices involved in operation of the instrument;

FIG. 2 is an enlarged longitudinal sectional view of the instrument of FIG. 1;

FIG. 3 is a sectional view, taken at 3—3 in FIG. 2; and

FIG. 4 is another sectional view, taken at 4—4 in FIG. 2.

The system of FIG. 1 is seen to comprise a hand-held instrument 10 that is centrally open at its distal end 11 and which is manipulable via a handle (a portion of which is suggested by phantom outline) 12 at its proximal end. Laser radiation from an external source 13, and pursuant to control at 14, is deliverable via an optical-fiber cable 15 that is centrally guided and positioned within the instrument for laser discharge at 16. The location of the fiber end 16 is within a shallow distally open cavity defined by and within a short cylindrical region 17 that is truncated at an angle α to provide a sharpened cutting edge at least in the region of its distally projecting limit 18. Provision is made for a controlled flow of infusion liquid from a source 19 to a first or outer annular cannula within the instrument, for ported external discharge near the distal end, and a second elongate cannula within the instrument communicates between the distal-cavity region 17 and an external evacuation system which includes a trap 41 for aspiration and accumulation of fragmented lens material.

Referring now to FIGS. 2 to 4, the operative portion of the instrument 10 will be seen to be contained within an outer annular cannula having a reduced but elongate cylindrical shell 20 which is exposed distally, and a slightly enlarged proximal-end shell 21, which has means of attachment to handle 12 (not shown in FIG. 2); FIG. 2 will be understood to have been longitudinally foreshortened for better showing of detail. The outer annular cannula is completed by an inner tubular member or shell 22 and by a distal-end closure wall 23 that is ported at spaced locations 24 (FIG. 4) for discharge of infusion liquid, such as a balanced saline solution. The proximal end of the outer cannula is closed by an annular plug or clamp fitting 25, removably secured by threaded engagement to the enlarged proximal-end member 21. For independent integrity of outer-cannula body structure, a frusto-conical element 26 connects outer shells 20, 21 to each other and to the inner tubular shell 22, and an angularly distributed plurality of ports 27 in the frusto-conical element accommodates flow of infusion liquid from an inlet fitting 28 to the discharge ports 24. Finally, the distal end of inner shell 22 is seen to have the previously described truncated and sharpened formation at 17, 18.

The inner cannula 30 is elongate and tubular, deriving guided support from the inner shell 22 of the outer cannula, and having a radial flange 31 at its proximal end such that, upon take-up of the threaded assembly of parts 21, 25 to each other, flange 31 is securely clamped, thus rigidly positioning the inner cannula 30, with its distal end forward of the closure wall 23 of the outer annular cannula. A local sector or strut formation 33 (FIGS. 3, 4) in the otherwise open bore of the inner cannula 30 extends longitudinally for central rigid positioning of a piloting tube 34, as of stainless steel, for guided retention of the optical-fiber cable 15. The optical-fiber cable 15 is protected at proximal-end entry into its guide tube, by a resilient elastomeric bushing 35, as of silicone rubber, carried locally by cannula 30 and having light frictional retaining engagement to cable 15, whereby to retain optical-fiber discharge of laser radiation at 16.

The open bore 36 of cannula 30 establishes a through inner passage which communicates from the distal shallow chamber 17 to a proximal chamber 37 defined by an end-bell portion 38 which, with the annular thread fitment 25, is a detachable subassembly to the enlarged shell 21 and to the inner cannula 30, at flange 31. The end-bell portion 38 is shown with a port fitment 39, adapted for slip-fitted flexible connection to the aspiration device 41. Finally, another elastomeric bushing 40 carried by end-bell 38 loosely and yieldingly provides central protection for the optical-fiber cable, at entry into the instrument.

Use of the described construction involves certain mechanical assembly operations. A sterilized length of optical-fiber cable 15 is threaded through the end-bell bushing 40, and then through the friction engagement of bushing 35 and with guidance by tube 34 until the distal end of the optical fiber is flush with the end of tube (34) support by strut 33. The thus-loaded inner cannula 30 is inserted into the bore of the outer cannula, until limited by its flange (31) engagement of the proximal end of the inner tubular member 22 of the outer cannula. The end-bell subassembly 25, 38, which may be a disposable item, is then thread-engaged to the outer cannula shell 21, thereby completing the mechanical assembly of the instrument, with the inner cannula securely clamped and retained. At this point, visual inspection and minor adjustment can assure correct distal-end positioning of the optical fiber of cable 15. Infusion tubing and aspiration tubing can then be connected, and the vacuum apparatus adjusted to a selected vacuum condition in the range of 100 to 500-mm Hg; the Alcon 10,000 I/V instrument is among those commercially available devices that can provide continuous or interrupted and variable aspiration. Infusion is usually produced by elevating the container 19 to a level between 10 and 65-cm above the level of the patient's eye, a simple gravity flow of infusion fluid being used to maintain intraocular pressure, and to provide liquid transport into the eye while aspiration is underway.

Operation of the thus-prepared instrument 10 is to be differentiated from the devices acknowledged above. Once the cataract is approached, cortical material can be cleared from the anterior surface of the lens, and the nucleus can be engaged by the sharpened truncation of the protruding end 18 of the outer cannula. A small quantity or chunk of cataractous tissue can then be manipulated into close approach to the shallow chamber region 17; if this small quantity does not aspirate directly, short bursts of pulsed laser energy can be directed at the cataractous tissue, e.g., at the rate of 1 to 25 pulses per second, to break-up the chunk and to transport its fragmented products remotely, by the aspiration mechanism, it being understood that laser energy need only be applied for break-up of lens tissue into smaller particles that can be handled by the aspiration system.

It is a feature of the invention that the particular laser shall be selected for use at 13, for its limited radiation wavelength at or close to one of high water-absorption peaks, e.g., at approximately 2.0, 3.0 and 6.0 microns, whereby laser-beam energy released into shallow chamber 17 is almost totally absorbed within a very short distance. For example, the beam from a Holmium-YAG laser operating at 2.10 microns, is virtually totally absorbed (i.e., 67% absorbed) within a distance of about 0.3-mm*, in a watery medium such as that of cataractous-lens tissue and the liquid environment provide by the described I/A flow. Another possible laser configuration at 13 is the Thulium-YAG laser**, which radiates at 2.01 microns, and which is 67 percent absorbed within 150 microns from the exit port 16 of the optical-fiber cable. There are other lasers that can be recited to serve the short dissipation-distance purposes of the invention, but it should be generally stated that the delivered laser radiation, emanating at 16 from the optical fiber, should meet the following criteria, all of which are met by the indicated Holmium and Thulium configurations:

a. The water-absorption coefficient should advisedly be at least 10 $cm^{-1}$.
b. The irradiated energy level should be in the range 1 to 350 millijoules/pulse.
c. The pulse-delivery rate for a given burst should be in the range 1 to 25 Hertz.
d. The burst duration should be selectively variable, by adjustment at control means 14, within the range 0.1 to 5 seconds.

*Absorption coefficient = 35-$cm^{-1}$
** Absorption coefficient = 70-$cm^{-1}$

What has been said for the above criteria applies to delivered or deliverable energy levels at the location 16 of radiation into the aqueous medium, i.e., after allowance for such attenuation as may be attributable to detachable coupling of cable 15 to laser 13 and to distributed attenuation along the length of cable 15.

The described invention will be seen to meet stated objects. When needed to break-up a chunk of cataractous tissue, the tissue can be fragmented by laser-energy levels which, by virtue of wavelength selection restricted to water-absorption properties, are inherently incapable of such penetration as might be in any way harmful to other tissues within the eye.* In other words, as long as the surgeon exercises normal caution to avoid instrument contact with the corneal endothelium and other components that are irrelevant to cataract surgery, and as long as he operates upon what he can see by operational-microscope viewing through a clear cornea and a dilated iris, the laser energy emanating at 16 is incapable of causing damage to the patient's eye. By contrast, it is indicated that the Neodymium-YAG radiation which is suitable for use in the closed-chamber embodiments of another U.S. patent application Ser. No. 07/732,801 filed on or about Jul. 19, 1991 has a water-absorption coefficient=0.8 cm$^{-1}$, involving an extremely high transmission of 12.5-mm in an aqueous environment.

What is claimed is:

1. Phaco-extractor means for fragmenting cataractous-lens tissue and for removing fragmented tissue from the situs of fragmentation, comprising an elongate hand-held instrument extending from a proximal hand-end region to a distal operating-end region, inner aspirating-tube means that is distally open at the distal operating-end region, irrigating means surrounding said aspirating-tube means and having discharge-porting for distally discharging a flow of irrigating liquid from a location that is near but short of the distal operating-end region, elongate optical-fiber means centrally supported within said inner aspirating-tube means and having a distal end for longitudinal discharge of laser energy from a central location that is axially short of said distal operating-end region; thereby establishing, for transient retention of a dislodged chunk of cataractous-lens tissue, a limited volumetric space defined proximally by the distal end of said optical-fiber means and distally by the distal operating-end region; and laser means coupled to said optical-fiber means for selectively controlled laser discharge at the distal end of said optical-fiber means, whereby to fragment a chunk of cataractous-lens tissue retained in said limited volumetric space, for more ready extraction via an aspirating flow in said inner aspirating-tube means, said laser means being selected for radiation at or close to one of the peak wavelengths of water absorption and having a water-absorption coefficient of at least 10 cm$^{-1}$.

2. The phaco-extractor means of claim 1, in which said laser means has a pulsed output and the irradiated energy level of said laser means is in the range 1 to 350 millijoules/pulse.

3. The phaco-extractor means of claim 2, in which the pulse-repetition rate for said pulsed output is in the range 1 to 25 Hz.

4. The phaco-extractor means of claim 3, in which said laser includes control means that is selectively variable to determine bursts of pulses, wherein a selected burst is in the range 0.1 to 5 seconds.

5. Phaco-extractor means according to claim 1, wherein said passages are defined by and radially between two elongate concentric annular cannulas, the inner one of said cannulas including means centrally supporting said fiber-optic delivery system.

6. Phaco-extractor means according to claim 5, in which said supporting means comprises an elongate guide tube sized for sliding guidance of a fiber-optic cable insertably receivable via the proximal end of said guide tube to the point of optical discharge at the distal end of said tube, and means including at least one radial strut within the inner cannula for radially positioning said tube.

7. Phaco-extractor means according to claim 1, in which said laser means is of a variety which radiates at a wavelength which is at or close to a high water-absorption peak.

8. Phaco-extractor means according to claim 1, in which said laser means is separate from said instrument, and said elongate optical-fiber means is a flexible optical-fiber cable detachably connected at one end to said laser means, with the other end of said cable extending within a guide tube, to an inserted position of fiber-end exposure at the distal end of said tube, said laser means being selected for its active lasing substance taken from the group comprising Holmium, Thulium, Erbium, Cobalt, and Magnesium.

9. Phaco-extractor means according to claim 8, wherein substrate material of said laser means is selected from the group comprising YAG, YLF, YSGG and glass.

10. Phaco-extractor means according to claim 1, in which the effective distal end of said aspirating-tube means is tubular at the distal operating-end region and projects distally beyond the discharge porting of said irrigating means, said projecting tubular distal end being truncated at an acute angle to the central axis of said projecting tubular distal end.

11. Phaco-extractor means according to claim 10, in which the distal truncation is characterized by a sharpened peripheral edge of tissue-cutting quality.

12. Phaco-extractor means for fragmenting cataractous-lens tissue and for removing fragmented tissue from the situs of fragmentation, comprising a hand-held instrument with elongate tubular means about a central axis and having a distal working end and a proximal manipulation end, said tubular means containing divider means for defining first and second elongate concentric annular cannulas each of which has at least one opening at the distal end, an infusion-port connection to one of said cannulas near the proximal manipulation end, an aspiration-port connection to the other of said cannulas near the proximal manipulation end, and laser means including a fiber-optic delivery system centrally supported by and within the inner one of said tubular means and terminating at said distal end for laser-energy discharge from said distal end; said tubular means including an internal annular wall at the proximal end, and said outer cannula comprising a subassembly of spaced inner and outer tubular members having removable connection to said wall and having a distal-end closure wall that has angularly spaced ports for infusion-liquid discharge.

13. Phaco-extractor means according to claim 12, in which said inner cannula comprises an elongate tube having a radially outward flange at its proximal end for abutment with said annular wall, the inner tubular member of said outer cannula having a concentric sliding engagement with said elongate tube and retaining said outward flange in clamped engagement with said annular wall when said subassembly is connected to said wall.

14. Phaco-extractor means according to claim 12, in which the inner tubular member of said subassembly projects distally beyond the outer tubular member of said subassembly, and in which the distal end of said inner tubular member is truncated at an acute angle to the central axis of said inner tubular member.

15. Phaco-extractor means according to claim 14, in which the truncation of said inner tubular member is characterized by a sharpened peripheral edge of tissue-cutting quality.

16. The method of performing phacoextraction of cataractous-lens tissue, using an elongate hand-held instrument extending from a proximal handle region to a distal-end region, wherein (a) the instrument has an inner aspirating tube that is open at its distal end and has provision for external aspiration in the proximal handle region, (b) a concentric outer irrigating tube with distal porting around the distal end of the aspirating tube and with provision for external supply of a flow of irrigation liquid near the proximal handle region, and (c) an optical-fiber cable centrally positioned within the inner tube for conveying laser energy from an external source via the proximal handle region to a point of laser-energy discharge that is centrally within and axially short of the distal open end of the inner aspirating tube, whereby to establish a limited volumetric space defined proximally by the distal end of the optical-fiber cable and distally by the distal end of the inner aspirating tube, said method comprising the steps of:

(1) entering the distal end of the instrument into an eye and fragmenting cataractous-lens tissue by manipulating the distal end of the instrument in contact with the cataractous-lens tissue to the point of lodging a chunk of cataractous-lens tissue at least in part within said volumetric space;

(2) delivering pulsed laser energy via the optical fiber cable at or close to one of the peak wavelengths of water absorption, wherein the laser energy radiated at the distal end of the optical-fiber cable has a water-absorption coefficient of at least 10 $cm^{-1}$; and wherein the delivered energy satisfies the following additional criteria:
  (a) irradiated energy level in the range 1 to 350 millijoules/pulse;
  (b) pulsed delivery being in a burst of pulses at a pulse-delivery rate in the range 1 to 25 Hertz; and
  (c) burst duration being in the range 0.1 to 5 seconds; whereby to locally further fragment at least a fraction of the lodged chunk for aspiration proximally via the inner tube; and (4) repeating delivery steps (2) and (3) if necessary until the lodged chunk has been sufficiently fragmented for removable aspiration, before manipulating the instrument to the point of lodging another chunk pursuant to step (1) and repeating step (2) until the cataractous tissue has been completely aspirated via the inner tube.

* * * * *